US012657701B2

(12) United States Patent
Higa

(10) Patent No.: US 12,657,701 B2
(45) Date of Patent: Jun. 16, 2026

(54) MEDICAL IMAGE PROCESSING DEVICE, OPERATION METHOD OF MEDICAL IMAGE PROCESSING DEVICE, AND RECORDING MEDIUM FOR ESTIMATING A STATE OF AN OBSERVATION IMAGED BY AN ENDOSCOPE

(71) Applicant: FUJIFILM Corporation, Tokyo (JP)

(72) Inventor: Katsuyuki Higa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 472 days.

(21) Appl. No.: 18/156,304

(22) Filed: Jan. 18, 2023

(65) Prior Publication Data

US 2023/0245304 A1 Aug. 3, 2023

(30) Foreign Application Priority Data

Feb. 1, 2022 (JP) ................................. 2022-014091

(51) Int. Cl.
*G06T 7/00* (2017.01)
*A61B 1/00* (2006.01)
(Continued)

(52) U.S. Cl.
CPC ...... *G06T 7/0012* (2013.01); *A61B 1/000094* (2022.02); *A61B 1/000096* (2022.02);
(Continued)

(58) Field of Classification Search
None
See application file for complete search history.

(56) References Cited

U.S. PATENT DOCUMENTS 9,503,692 B2 11/2016 Morita et al.
11,379,977 B2 * 7/2022 Endo .................. A61B 1/00055
(Continued)

FOREIGN PATENT DOCUMENTS

JP H09-26547 A 1/1997
JP 2004-188026 A 7/2004
(Continued)

OTHER PUBLICATIONS

International Search Report (Form PCT/ISA/210) of PCT/JP2018/038061, mailed on Nov. 13, 2018.
(Continued)

*Primary Examiner* — Tahmina N Ansari
(74) *Attorney, Agent, or Firm* — Studebaker Brackett PLLC

(57) ABSTRACT

Provided are a medical image processing device, an operation method of the medical image processing device, a medical image processing program, and a recording medium that are capable of accurately estimating a state of the observation region of an observation image captured by an endoscope.

In the medical image processing device including a processor 22, an image acquisition unit 110 of the processor 22 acquires an observation image 100 in which an observation region in a body is imaged by an endoscope. A distance information-acquisition unit 112 of the processor 22 acquires (estimates) distance information regarding a distance between the endoscope and the observation region from the observation image 100. A state estimation unit 114 of the processor 22 estimates a state of the observation region based on the observation image 100 and the distance information.

14 Claims, 14 Drawing Sheets

(51) Int. Cl.
    *G06T 7/50* (2017.01)
    *G06V 10/764* (2022.01)
(52) U.S. Cl.
    CPC .............. *G06T 7/50* (2017.01); *G06V 10/764*
        (2022.01); *G06T 2207/10068* (2013.01); *G06T*
        *2207/20081* (2013.01); *G06T 2207/30096*
                                        (2013.01)

(56)               References Cited

U.S. PATENT DOCUMENTS

| | | | |
|---|---|---|---|
| 11,379,997 B2 * | 7/2022 | Lee ........................... G06T 5/70 |
| 2005/0207645 A1 | 9/2005 | Nishimura et al. |
| 2006/0280347 A1 | 12/2006 | Shirahata et al. |
| 2015/0320296 A1 | 11/2015 | Morita |
| 2016/0042122 A1 | 2/2016 | Sato et al. |
| 2018/0098690 A1 | 4/2018 | Iwaki |
| 2020/0242766 A1 * | 7/2020 | Endo ................... A61B 1/0655 |
| 2021/0133986 A1 * | 5/2021 | Lee ........................... G06T 5/77 |
| 2021/0161363 A1 * | 6/2021 | Makino ................. G06N 3/084 |
| 2021/0374990 A1 | 12/2021 | Miyashita et al. |
| 2022/0095889 A1 | 3/2022 | Sato |
| 2022/0277449 A1 * | 9/2022 | Endo ................... A61B 1/0004 |
| 2022/0293268 A1 | 9/2022 | Nishide |
| 2022/0358750 A1 | 11/2022 | Tsujimoto |
| 2022/0383533 A1 | 12/2022 | Takenouchi |
| 2023/0169669 A1 * | 6/2023 | Kamijo .............. A61B 1/00055 600/103 |
| 2023/0172682 A1 * | 6/2023 | Krieger .................. A61B 90/04 606/20 |
| 2023/0245304 A1 * | 8/2023 | Higa ................ A61B 1/000094 382/128 |
| 2023/0268041 A1 * | 8/2023 | Grady .................... G16H 50/20 705/2 |
| 2023/0277036 A1 * | 9/2023 | Yumbe ...................... G06T 7/00 348/65 |
| 2024/0013389 A1 | 1/2024 | Usuda |
| 2024/0293000 A1 * | 9/2024 | Higa ........................ A61B 1/05 |

FOREIGN PATENT DOCUMENTS

| | | | |
|---|---|---|---|
| JP | 2006-129950 A | 5/2006 |
| JP | 2009-072369 A | 4/2009 |
| JP | 2011-104016 A | 6/2011 |
| JP | 2012-000291 A | 1/2012 |
| JP | 2014-188222 A | 10/2014 |
| JP | 3194808 U | 12/2014 |
| JP | 2016-045573 A | 4/2016 |
| JP | 2016-062488 A | 4/2016 |
| JP | 2016-172077 A | 9/2016 |
| JP | 2020-156903 A | 10/2020 |
| JP | 2021-189822 A | 12/2021 |
| WO | 2005/11501 A1 | 2/2005 |
| WO | 2016/199273 A1 | 12/2016 |
| WO | 2021/141048 A1 | 7/2021 |
| WO | 2021/157487 A1 | 8/2021 |
| WO | 2021/205818 A1 | 10/2021 |
| WO | 2022/202520 A1 | 9/2022 |

OTHER PUBLICATIONS

Written Opinion of the International Searching Authority (Form PCT/ISA/237) of PCT/JP2018/038061, mailed on Nov. 13, 2018.
An Office Action; "Notice of Reasons for Refusal," mailed by the Japanese Patent Office on Oct. 27, 2020, which corresponds to Japanese Patent Application No. 2019-549239; with English language translation.
An Office Action; "Notice of Reasons for Refusal," mailed by the Japanese Patent Office on Aug. 3, 2021, which corresponds to Japanese Patent Application No. 2019-549239; with English language translation.
An Office Action mailed by the United States Patent and Trademark Office on Sep. 3, 2021, which corresponds to U.S. Appl. No. 18/156,304, and is related to U.S. Appl. No. 18/156,304.
"Notice of Reasons for Refusal" Office Action issued in JP 2022-014091; mailed by the Japanese Patent Office on Jul. 23, 2025.
The extended European search report issued by the European Patent Office on Jul. 15, 2024, which corresponds to European Patent Application No. 24159475.3-1122, all pages.

* cited by examiner

[DISTANCE MAP]

[OBSERVATION IMAGE]

[NEAR VIEW MODE]

[DISTANT VIEW MODE]

FIG. 8B

[DISTANCE MAP]

FIG. 8A

[MODE SWITCHING AT SMALL REGION LEVEL]

[DISTANCE MAP]

LOW ACCURACY

HIGH ACCURACY

THRESHOLD VALUE A

THRESHOLD VALUE B

DISTANT

NEAR

MEDICAL IMAGE PROCESSING DEVICE, OPERATION METHOD OF MEDICAL IMAGE PROCESSING DEVICE, AND RECORDING MEDIUM FOR ESTIMATING A STATE OF AN OBSERVATION IMAGED BY AN ENDOSCOPE

CROSS-REFERENCE TO RELATED APPLICATION

The present application claims priority under 35 U.S.C § 119(a) to Japanese Patent Application No. 2022-014091 filed on Feb. 1, 2022, which is hereby expressly incorporated by reference, in its entirety, into the present application.

BACKGROUND OF THE INVENTION

1. Field of the Invention

The present invention relates to a medical image processing device, an operation method of the medical image processing device, a medical image processing program, and a recording medium, and particularly, relates to a technology for favorably estimating a state of an observation region from an observation image in which the observation region in a body is imaged by an endoscope.

2. Description of the Related Art

Conventionally, in order to prevent an oversight of a lesion during an endoscopy, the lesion is automatically detected and notified by an artificial intelligence (AI) or the like. In addition, there is also a discrimination AI for determining whether the detected lesion is truly a lesion.

In JP2020-156903A, an endoscope processor having a high ability to detect a lesion is proposed.

The endoscope processor described in JP2020-156903A generates a first processed image and a second processed image obtained by performing different image processing on the captured image captured by the endoscope, and outputs, using a learning model in which the generated first processed image and second processed image are input, a disease state which is an estimation result of the learning model.

In addition, JP2020-156903A describes that a learning model is generated for each disease of a diagnosis target or a learning model is generated for each part of the diagnosis target. A user selectively instructs which disease is to be diagnosed or which part is to be diagnosed, and the endoscope processor uses a learning model corresponding to the user's selection instruction to output the disease state.

SUMMARY OF THE INVENTION

However, in a case of estimating a state of an observation region (for example, the presence or absence of a lesion) from an observation image in which an observation region in a body is imaged by an endoscope, an estimation performance of the state of the observation region deteriorates depending on an imaging distance of the observation image. It is considered that this is because the appearance of the observation image differs depending on the imaging distance.

The present invention has been made in consideration of such circumstances, and an object thereof is to provide a medical image processing device, an operation method of the medical image processing device, a medical image processing program, and a recording medium that are capable of accurately estimating a state of the observation region of the observation image captured by the endoscope.

In order to achieve the above object, the present invention according to a first aspect is a medical image processing device including a processor. The processor acquires an observation image in which an observation region in a body is imaged by an endoscope, acquires distance information regarding a distance from the endoscope to the observation region, and estimates a state of the observation region based on the observation image and the distance information.

According to the first aspect of the present invention, in a case of estimating the state of the observation image from the observation image in which the observation region in the body is imaged by the endoscope, it is possible to accurately estimate the state of the observation region regardless of the imaging distance of the observation image by also using the distance information regarding the distance from the endoscope to the observation region.

In the medical image processing device according to a second aspect of the present invention, it is preferable that the processor selects any estimation mode among a plurality of estimation modes for estimating the state of the observation region based on the acquired distance information, and estimates the state of the observation region by the selected estimation mode.

In the medical image processing device according to a third aspect of the present invention, it is preferable that the processor weight-averages estimation results of the state of the observation region respectively estimated by a plurality of estimation modes for estimating the state of the observation region according to the acquired distance information to obtain a final output.

Accordingly, it is possible to weight-average the estimation results of the state of the observation region respectively estimated by the plurality of estimation modes by using the optimum weighting coefficient, and the state of the observation region can be favorably estimated from the weighted average.

In the medical image processing device according to a fourth aspect of the present invention, it is preferable that the plurality of estimation modes include a near view mode in which the state of the observation region is estimated based on the observation image and a distant view mode in which the state of the observation region is estimated based on the observation image, and of which an accuracy of estimating the state of the observation region is higher than that of the near view mode in a case where the distance information exceeds a threshold value. Since the appearance of the observation image differs depending on the distance, it is preferable to apply an estimation mode (near view mode, distant view mode) suitable for the distance of the observation image.

In the medical image processing device according to a fifth aspect of the present invention, it is preferable that a first learning model that uses the observation image as an input and estimates the state of the observation region corresponding to the near view mode, and a second learning model that uses the observation image as an input and estimates the state of the observation region corresponding to the distant view mode are provided, and the processor estimates the state of the observation region using at least one of the first learning model or the second learning model.

In the medical image processing device according to a sixth aspect of the present invention, it is preferable that the plurality of estimation modes include a detection mode in which a lesion existing in the observation region is detected based on the observation image, and a discrimination mode in which the lesion existing in the observation region is classified into two or more types of classes based on the observation image.

In the medical image processing device according to a seventh aspect of the present invention, it is preferable that the observation image includes a normal light image captured by using normal light and a special light image captured by using special light, and the processor acquires an observation mode indicating whether the observation image is the normal light image or the special light image together with the distance information of the observation image, and selects the detection mode or the discrimination mode based on the distance information and the observation mode. Since the appearances of the normal light image and the special light image are different, it is preferable that the information of these images is also used for selecting the detection mode or the discrimination mode.

In the medical image processing device according to an eighth aspect of the present invention, it is preferable that the processor selects the discrimination mode in a case where the distance information is equal to or less than a threshold value and the observation mode is a special light observation mode for observing the special light image.

In the medical image processing device according to a ninth aspect of the present invention, it is preferable that the processor acquires each of pieces of the distance information corresponding to a plurality of small regions in the observation region, and estimates each of states of the plurality of small regions in the observation region based on the observation image and the pieces of distance information corresponding to the plurality of small regions. The small region may be one pixel of the observation image or may be a region of a plurality of pixels.

In the medical image processing device according to a tenth aspect of the present invention, it is preferable that a third learning model that uses the observation image as an input and estimates the distance information is provided, and the processor inputs the acquired observation image to the third learning model and acquires the distance information estimated by the third learning model. Since the distance information is acquired from the observation image, physical distance measurement using a laser beam for distance measurement is not required, and it is possible to acquire the distance information of the observation region in the observation image even with the endoscope that is difficult to mount a new measuring instrument.

In the medical image processing device according to an eleventh aspect of the present invention, it is preferable that a fourth learning model that uses at least one of a distance map showing the distance information of the observation region of the observation image or the observation image as an input and outputs a weighting coefficient used in calculation of the weighted average is provided, and the processor inputs at least one of the distance map or the observation image to the fourth learning model, and acquires the weighting coefficient used in the calculation of the weighted average from the fourth learning model.

In the medical image processing device according to a twelfth aspect of the present invention, it is preferable that the processor causes a display device that displays the observation image to display the estimated state of the observation region.

In the medical image processing device according to a thirteenth aspect of the present invention, it is preferable that the processor detects a lesion existing in the observation region as the state of the observation region, classifies the lesion existing in the observation region into two or more types of classes, and recognizes a treatment tool existing in the observation region or recognizes an organ or a part existing in the observation region.

The present invention according to a fourteenth aspect is an operation method of a medical image processing device including a processor, the method including: a step of acquiring an observation image in which an observation region in a body is imaged by an endoscope by the processor; a step of acquiring distance information regarding a distance from the endoscope to the observation region by the processor; and a step of estimating a state of the observation region based on the observation image and the distance information by the processor.

In the operation method of a medical image processing device according to a fifteenth aspect of the present invention, it is preferable that the step of estimating the state of the observation region includes a step of selecting any estimation mode among a plurality of estimation modes for estimating the state of the observation region based on the acquired distance information, and a step of estimating the state of the observation region by the selected estimation mode.

In the operation method of a medical image processing device according to a sixteenth aspect of the present invention, it is preferable that in the step of acquiring the distance information, each of pieces of the distance information corresponding to a plurality of small regions in the observation region is acquired, and in the step of estimating the state of the observation region, each of states of the plurality of small regions in the observation region is estimated based on the observation image and the pieces of distance information corresponding to the plurality of small regions.

The present invention according to a seventeenth aspect is a medical image processing program that causes a computer to execute the operation method of a medical image processing device according to any one of the fourteenth aspect to the sixteenth aspect.

The present invention according to an eighteenth aspect is a non-transitory computer-readable recording medium on which the medical image processing program according to the seventeenth aspect is recorded.

According to the present invention, it is possible to accurately estimate the state of the observation region from the observation image in which the observation region in the body is imaged by the endoscope, regardless of the imaging distance of the observation image.

BRIEF DESCRIPTION OF THE DRAWINGS

FIGS. 4A and 4B are diagrams showing an observation image and an example of a distance map acquired from the observation image.

FIGS. 8A and 8B are diagrams showing an example of an observation image to which mode switching is applied in the observation image and a distance map showing distance information of an observation region of the observation image.

FIGS. 10A to 10C are diagrams showing an example of a user interface in a case where a user sets a switching pattern between the near view mode and the distant view mode.

DESCRIPTION OF THE PREFERRED EMBODIMENTS

Hereinafter, preferred embodiments of a medical image processing device, an operation method of the medical image processing device, a medical image processing program, and a recording medium according to an embodiment of the present invention will be described with reference to the accompanying drawings.

System Configuration

Figure 1:
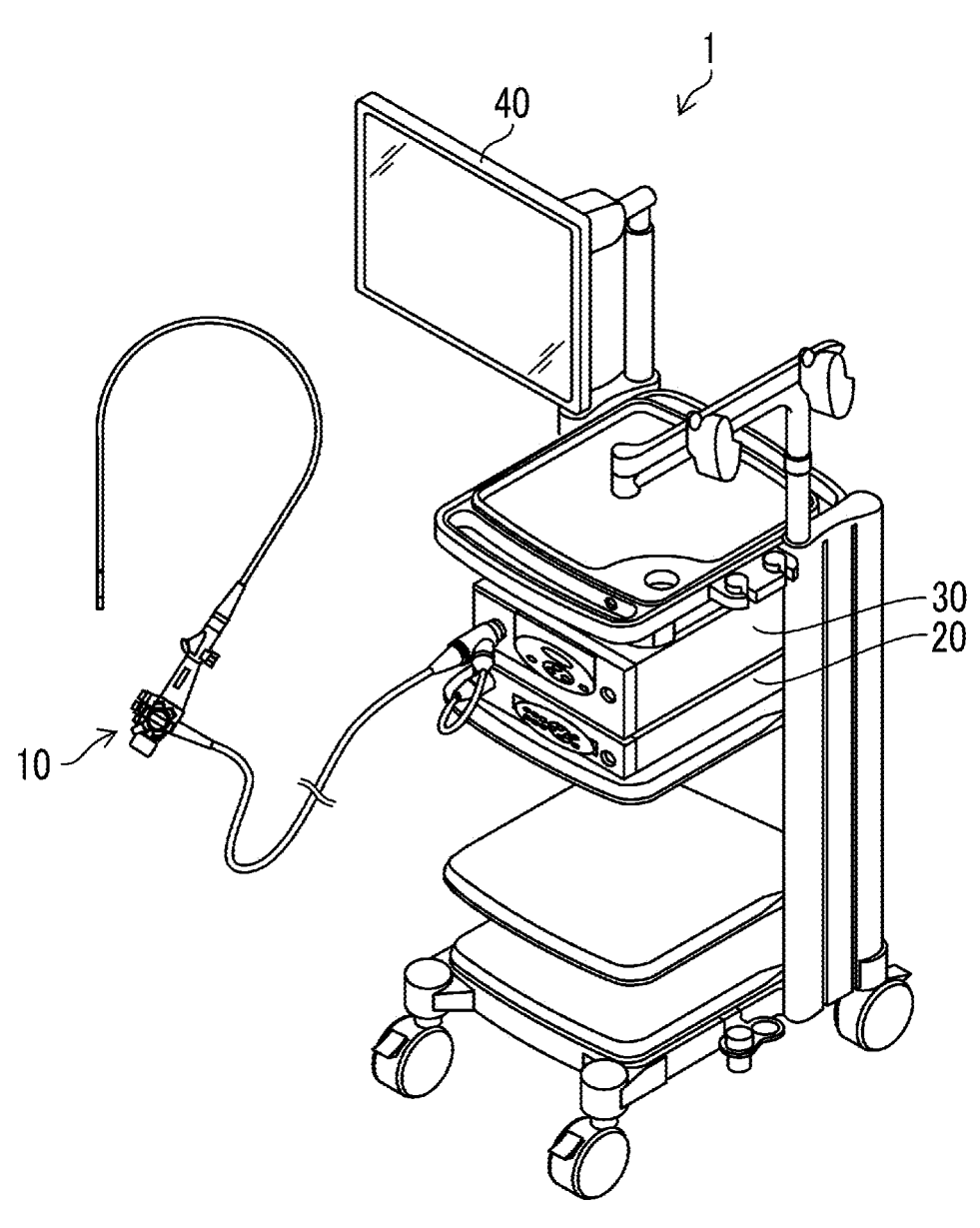
FIG. 1 is a system configuration diagram of an endoscope system including a processor device that functions as a medical image processing device according to the present invention.

FIG. 1 is a system configuration diagram of an endoscope system including a processor device that functions as a medical image processing device according to the embodiment of the present invention.

In FIG. 1, an endoscope system 1 is composed of an endoscope 10, a processor device 20, a light source device 30, and a display device 40.

The endoscope 10 is also referred to as an electronic endoscope or an endoscope scope. In addition, the endoscope 10 includes a laparoscope.

The endoscope 10 images an observation region in a body of a subject and acquires an endoscope image (hereinafter, referred to as an "observation image") which is a medical image. An optical system (objective lens), an imaging element, or the like is incorporated in a distal end part of the endoscope 10, and image light from the observation region is incident into the imaging element through the objective lens. The imaging element converts the image light of the observation region incident on an imaging surface into an electric signal, and outputs an image signal indicating the observation image.

A video connector and a light guide connector for connecting the endoscope 10 to the processor device 20 and the light source device 30 are provided at a rear end part of the endoscope 10. By mounting the video connector provided in the endoscope 10 to the processor device 20, an image signal indicating an observation image captured by the endoscope 10 is transmitted to the processor device 20. In addition, by mounting the light guide connector provided in the endoscope 10 to the light source device 30, an illumination light emitted from the light source device 30 is emitted from an illumination window on a distal end surface of the endoscope 10 toward the observation region through the light guide connector and a light guide disposed in the endoscope 10.

The light source device 30 supplies the illumination light to the light guide of the endoscope 10 through the light guide connector for the endoscope 10 to which the light guide connector is mounted. The light source device 30 can emit normal light (wideband white light or a plurality of pieces of wideband light having different wavelength bands) in accordance with an observation mode selected by the user (for example, a normal light observation mode, a special light observation mode, or the like), or it is possible to emit one or more pieces of special light (light in a specific narrow band, or light in various wavelength bands depending on an observation purpose such as a combination thereof).

In addition, in a case where the normal light is emitted from the light source device 30, the endoscope 10 can capture a normal light image (white light (WL) image), and in a case where the special light is emitted from the light source device 30, the endoscope 10 can capture a special light image (blue light imaging or blue laser imaging (BLI) image or a linked color imaging (LCI) image).

The special light for BLI is observation light in which a ratio of violet (V) light having a high absorption rate in superficial blood vessels is high and a ratio of green (G) light having a high absorption rate in intermediate blood vessels is suppressed. It is suitable for generating an image (BLI image) suitable for enhancing a blood vessel or a structure of a mucosal surface layer of the subject.

In addition, the special light for LCI has a higher ratio of V light than the observation light for WL, and is observation light suitable for capturing a minute change in color tone as compared with the observation light for WL. The LCI image is an image obtained by performing color enhancement processing such that a reddish color becomes redder and a whitish color becomes whiter, centering on a color in the vicinity of the mucous membrane using the signal of the red (R) component.

Processor Device

Figure 2:
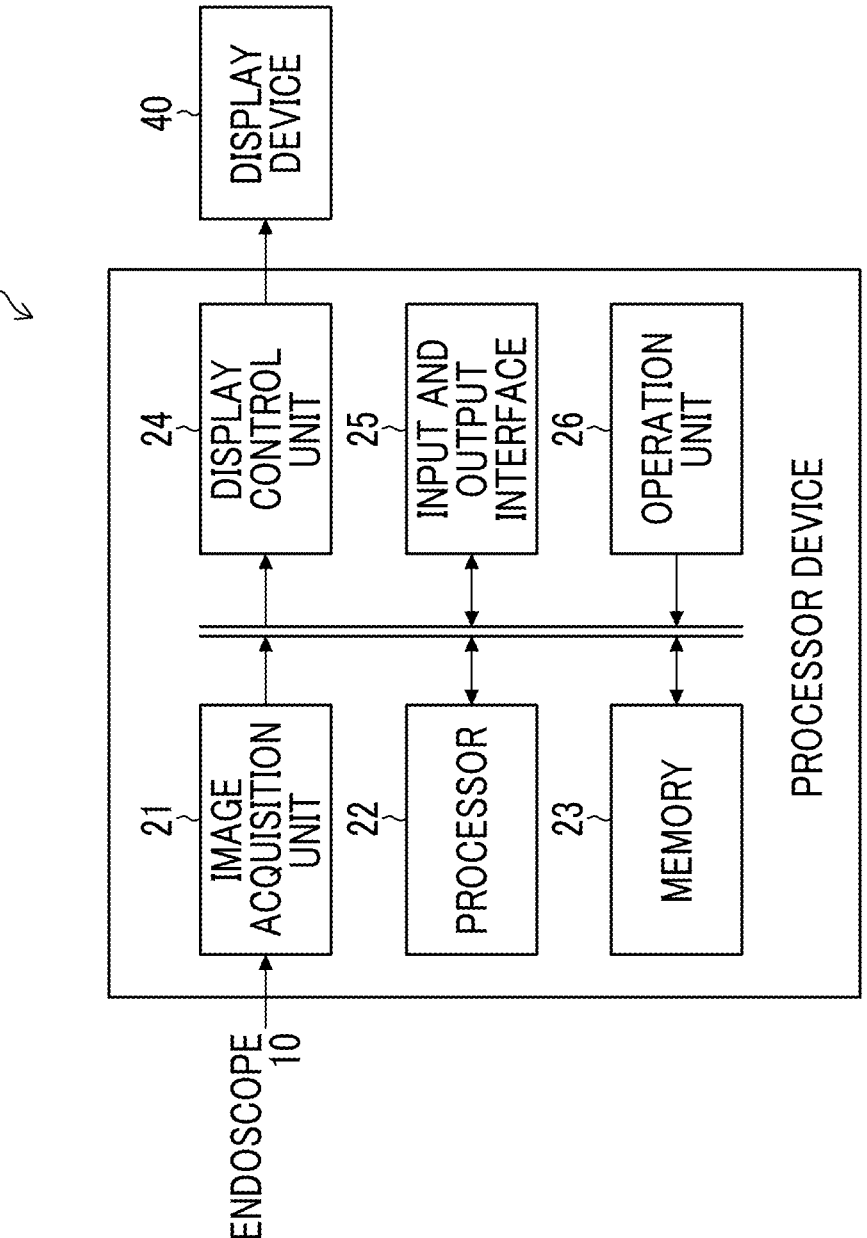
FIG. 2 is a block diagram showing an embodiment of a hardware configuration of the processor device constituting the endoscope system shown in FIG. 1.

FIG. 2 is a block diagram showing an embodiment of a hardware configuration of the processor device constituting the endoscope system shown in FIG. 1.

The processor device 20 shown in FIG. 2 is composed of an image acquisition unit 21, a processor 22, a memory 23, a display control unit 24, an input and output interface 25, and an operation unit 26.

The image acquisition unit 21 includes a connector to which a video connector of the endoscope 10 is connected, and acquires an observation image captured by an imaging element disposed at the distal end part of the endoscope 10 from the endoscope 10 through the connector. In addition, the processor device 20 acquires a remote signal operated by the hand operation unit of the endoscope 10 through a connector to which the endoscope 10 is connected. The remote signal includes a release signal instructing the still image capturing, an observation mode signal indicating an observation mode, and the like.

The observation image may be a moving image or a still image captured in synchronization with the release signal.

The processor 22 is composed of a central processing unit (CPU) and the like, controls each part of the processor device 20 in an integrated manner, and functions as a processing unit that performs image processing of the observation image acquired from the endoscope 10, artificial intelligence (AI) processing that estimates a state of the observation region from the observation image, processing of acquiring distance information regarding a distance from the endoscope 10 to the observation region, and acquisition and storage processing of a still image by a release signal acquired through the endoscope 10.

The memory 23 includes a flash memory, a read-only memory (ROM), a random access memory (RAM), a hard disk device, and the like. The flash memory, ROM, or hard disk device is a non-volatile memory that stores various programs and the like executed by the processor 22. The RAM functions as a work region for processing by the processor 22, and temporarily stores a program and the like stored in the flash memory and the like. The processor 22 may incorporate a part (RAM) of the memory 23. In addition, the still image captured during the endoscopy can be stored in the memory 23.

The display control unit 24 generates a display image based on an observation image (moving image or still image) after image processing added from the processor 22 and an estimation result of a state of the observation region subjected to the AI processing by the processor 22, and outputs the display image to a display device 40.

The input and output interface 25 includes a connection unit that connects to an external device by wire and/or wirelessly, a communication unit that is connectable to a network, and the like. By transmitting the observation image to the external device such as a personal computer connected through the input and output interface 25, the external device may have a part or all of the functions of the medical image processing device according to the embodiment of the present invention.

In addition, a foot switch (not shown) is connected to the input and output interface 25. The foot switch is an operation device that is placed at the feet of the operator and is operated by the foot, and the operation signal is transmitted to the processor device 20 by depressing the pedal. The processor device 20 is connected to a storage (not shown) through the input and output interface 25. The storage (not shown) is an external storage device connected to the processor device 20 through a local area network (LAN) or the like, and is, for example, a file server of a system for filing a medical image such as a picture archiving and communication system (PACS) and network attached storage (NAS).

The operation unit 26 includes a power switch, a switch for manually adjusting the white balance, the amount of light, zooming, and the like, a switch for setting an observation mode, and the like.

First Embodiment of Processor

Figure 3:
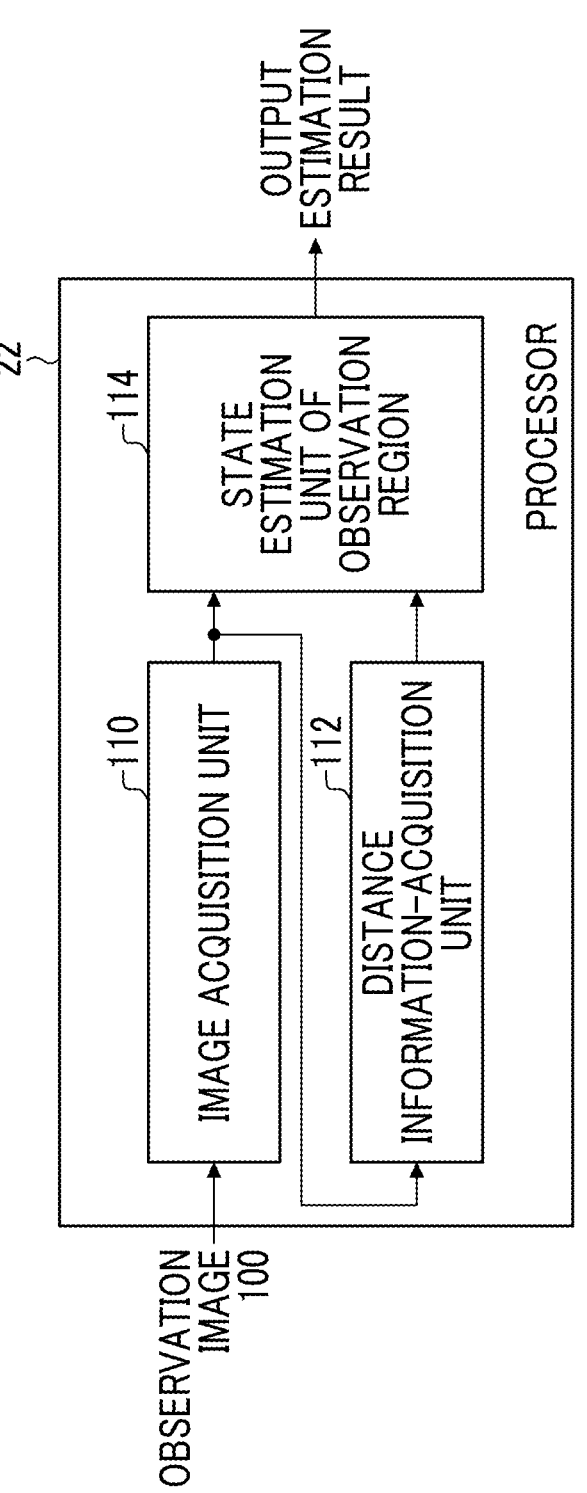
FIG. 3 is a functional block diagram showing a first embodiment of a main processor of the processor device shown in FIG. 2.

FIG. 3 is a functional block diagram showing a first embodiment of a main processor of the processor device shown in FIG. 2.

As shown in FIG. 3, the processor 22 comprises an image acquisition unit 110, a distance information-acquisition unit 112, and a state estimation unit 114 of an observation region.

The image acquisition unit 110 is a portion where the image acquisition unit 21 of the processor device 20 acquires the observation image 100 acquired from the endoscope 10. The image acquisition unit 21 of the processor device 20 is a hardware portion that acquires the observation image 100 from the endoscope 10, and the image acquisition unit 110 of the processor 22 is a software portion that acquires the observation image 100 to be processed by the distance information-acquisition unit 112 and the state estimation unit 114 in the subsequent stage. Therefore, the image acquisition unit 110 includes a case where the observation image 100 temporarily stored in the memory 23 is acquired from the memory 23.

The distance information-acquisition unit 112 is a portion that inputs the observation image 100 acquired by the image acquisition unit 110, and acquires distance information related to a distance from the endoscope 10 (distal end part) to the observation region based on the input observation image 100.

The distance information-acquisition unit 112 of this example uses a learning model (third learning model) that estimates the distance information, inputs the observation image 100 to the third learning model, and acquires the distance information estimated by the third learning model.

Figures 4A, 4B:
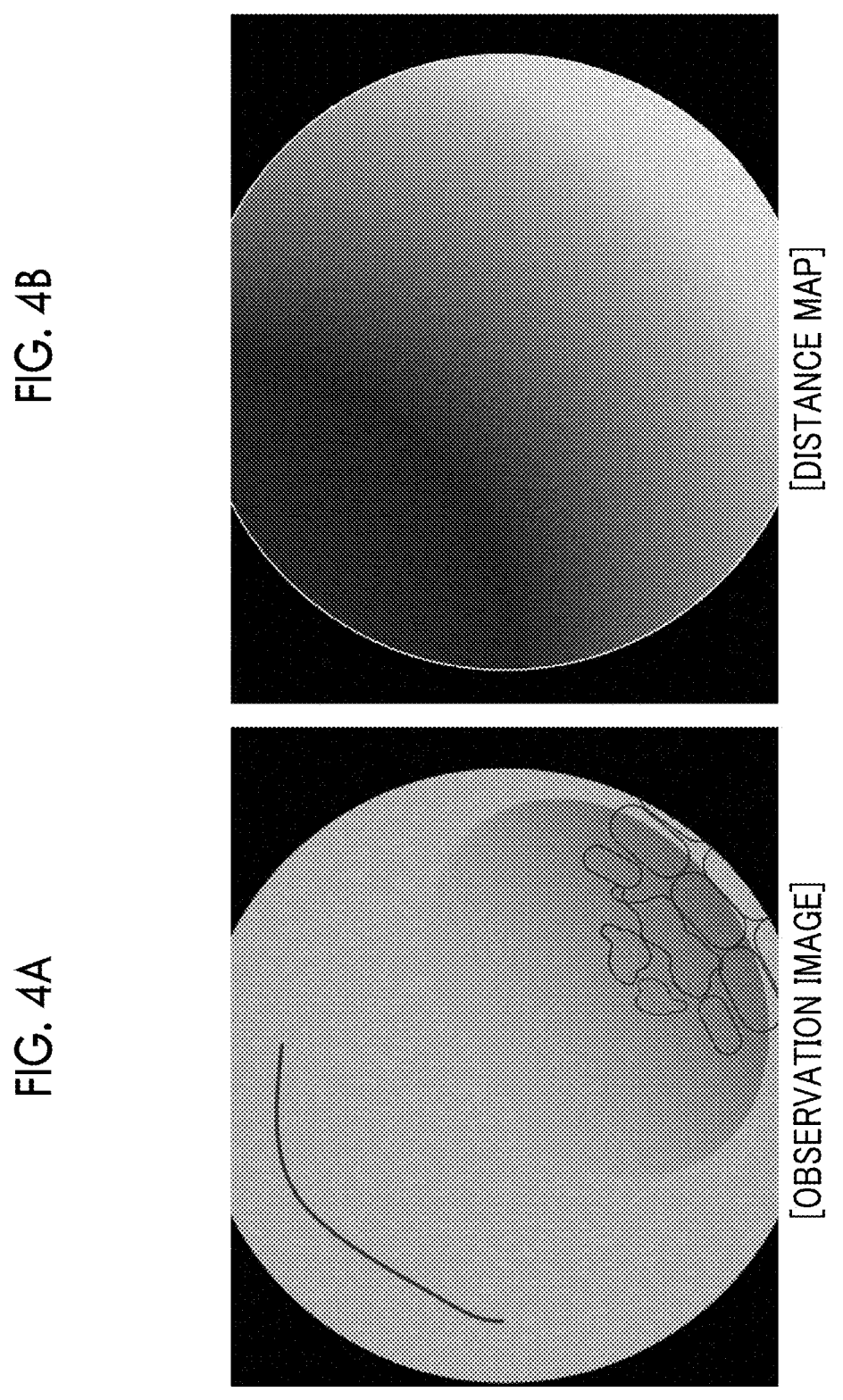

FIGS. 4A and 4B are diagrams showing an observation image and an example of a distance map acquired from the observation image.

FIG. 4A shows an observation image input to the fourth learning model used by the distance information-acquisition unit 112, and FIG. 4B shows an example of a distance map showing a distance estimation result estimated by the fourth learning model.

In the distance map shown in FIG. 4B, pixel values are assigned that become blacker as the distance from the endoscope 10 to the observation region increases and become whiter as the distance decreases.

The third learning model used by the distance information-acquisition unit 112 can apply a learned generator learned without a teacher using a large number of observation images in a generative adversarial network (GAN) having a generator and a discriminator. A fourth learning model is not limited to the generator learned by GAN, and may be learned by, for example, a variational auto encoder (VAE).

The observation image 100 acquired by the image acquisition unit 110 and the distance information acquired (estimated) by the distance information-acquisition unit 112 from the observation image 100 are added to the state estimation unit 114 of the observation region, and the state estimation unit 114 of the observation region estimates the state of the observation region based on the observation image 100 and the distance information.

Figure 5:
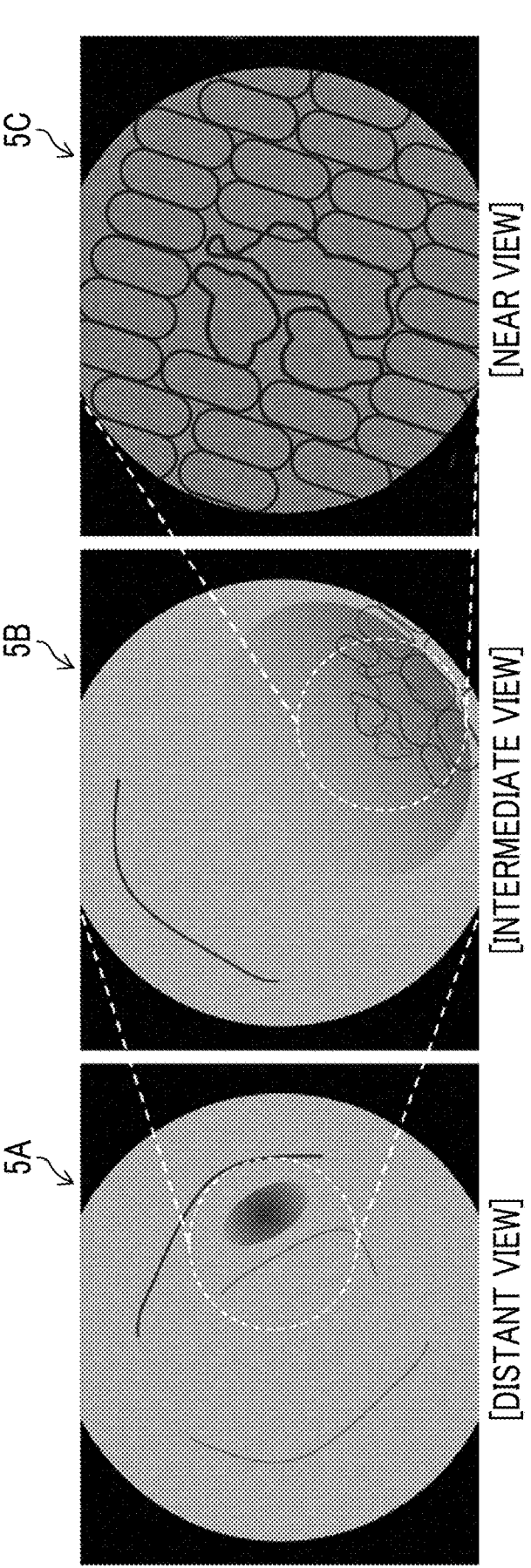
FIG. 5 is a diagram showing an example of observation images of a distant view, an intermediate view, and a near view.

FIG. 5 is a diagram showing an example of observation images of a distant view, an intermediate view, and a near view.

The appearance of the mucous membrane in the observation region to be observed with an endoscope may differ greatly depending on the distance thereof even at the same part.

FIG. 5 shows the appearance in a case of observing a certain lesion in a distant view, an intermediate view, and a near view. The characteristics of the lesion at each distance are as follows.

5A of FIG. 5 is an observation image of the distant view. From this observation image of the distant view, it is possible to observe an elliptical lesion having a strong redness (a portion having a high density on 5A of FIG. 5) as compared with the surroundings.

5B of FIG. 5 is an observation image of the intermediate view, and is an image obtained by capturing a circular region surrounding a lesion included in the observation image of the distant view in 5A of FIG. 5. From this observation image of the intermediate view, it is possible to observe a strong redness (a portion having a high density on 5B of FIG. 5) and an irregularity of the mucous membrane pattern as compared with the surroundings.

5C of FIG. 5 is an observation image of a near view, and is an image obtained by capturing a circular region surrounding a lesion included in the observation image of the intermediate view in 5B of FIG. 5. From this observation image of the near view, it is possible to observe the irregularities in the mucous membrane pattern over the entire image.

In this way, even for the same lesion, the characteristics exhibited differ depending on the imaging distance of the lesion. Therefore, it is unsuitable to estimate the state of the observation region including the detection and discrimination of the lesion by the same AI at all distances.

Therefore, the state estimation unit 114 of the observation region selects any estimation mode from a plurality of estimation modes for estimating the state of the observation region based on the distance information acquired from the distance information-acquisition unit 112 and estimates the state of the observation region by the selected estimation mode, or weight-averages the estimation results of the state of the observation region respectively estimated by the plurality of estimation modes that estimate the state of the observation region according to the acquired distance information to obtain the final output.

Here, "estimation of the state of the observation region" includes presence or absence of a lesion existing in the observation region and/or detection (estimation) of the lesion region, classification of two or more types of classes of lesions existing in the observation region (for example, neoplastic, non-neoplastic), recognition of the treatment tool existing in the observation region (presence or absence of treatment tool and/or recognition of type of treatment tool), or recognition of an organ or a part existing in the observation region. In a case where the endoscope 10 is an upper gastrointestinal endoscope, recognition of the organ existing in the observation region means detection (classification) of organs such as the esophagus, stomach, and duodenum. In addition, the recognition of the part means, for example, in a case where the organ is the stomach, detection of each part of the stomach such as the cardia, the stomach fundus, the upper stomach body, the middle stomach body, the lower stomach body, the vestibule, the pyloric vestibule, and the pylorus.

Hereinafter, in this example, a case where a lesion region existing in the observation region is detected (estimated) will be described as "estimation of the state of the observation region".

Specific Example of Processor of First Embodiment

Figure 6:
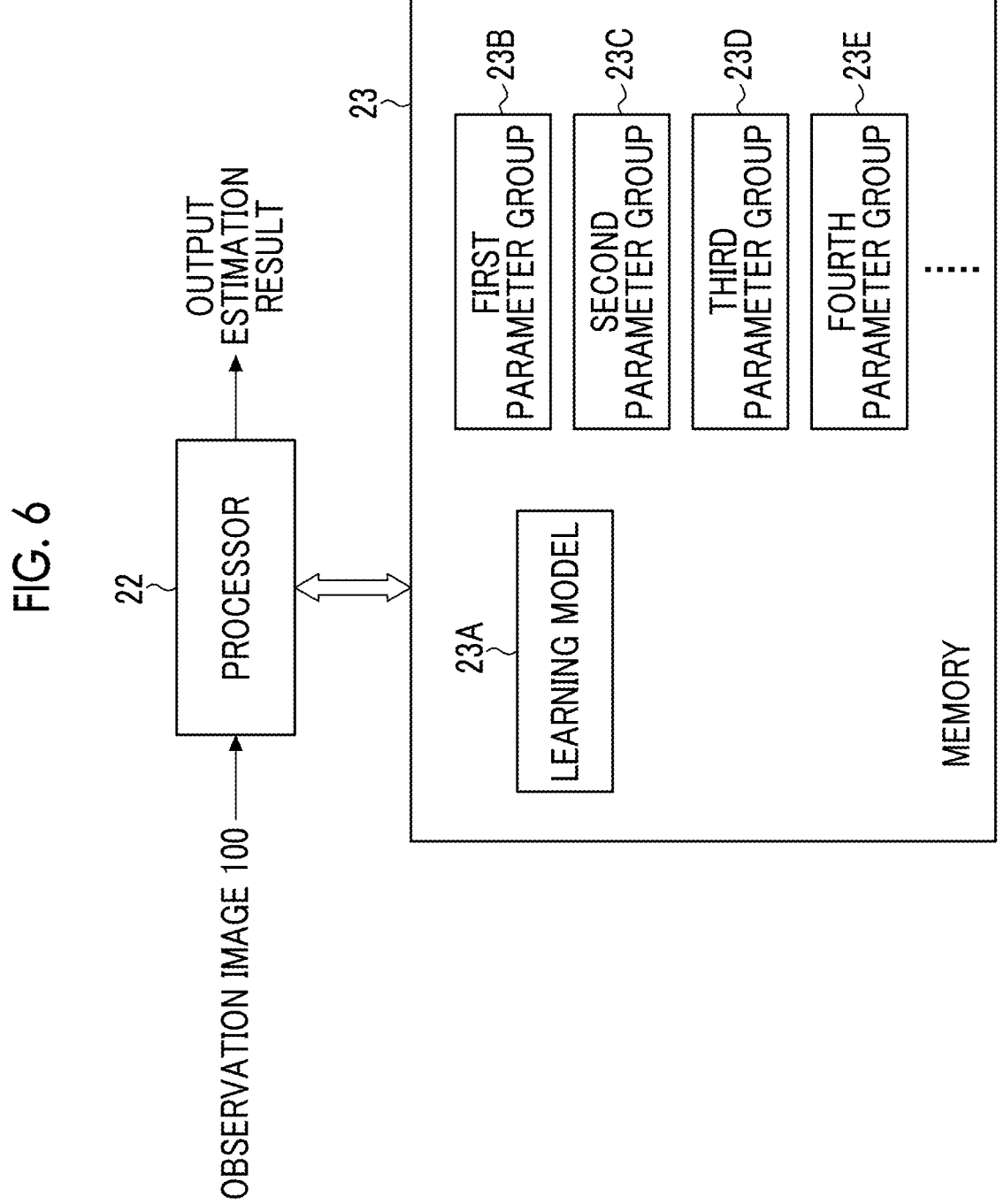
FIG. 6 is a block diagram showing a specific example of the processor shown in FIG. 3.

FIG. 6 is a block diagram showing a specific example of the processor shown in FIG. 3.

As shown in FIG. 6, the observation image 100 is input to the processor 22. The processor 22 reads out the learning model 23A and the necessary parameter group from the input observation image 100, the learning model 23A stored in the memory 23 in advance, the first parameter group 23B, the second parameter group 23C, the third parameter group

23D, the fourth parameter group 23E, and the like, and functions as the distance information-acquisition unit 112 and the state estimation unit 114 of the observation region shown in FIG. 3.

One or more known learning models can be applied as the learning model 23A, and for example, a convolution neural network (CNN) can be applied to the learning model used as the state estimation unit 114.

In addition, the first parameter group 23B, the second parameter group 23C, the third parameter group 23D, the fourth parameter group 23E, and the like are applied to one or more learning models 23A, and are, for example, a filter coefficient of the filter used in a convolutional layer of the CNN, a weight coefficient for input of each layer of the CNN, and the like.

The processor 22 applies the third parameter group to the learning model 23A read from the memory 23 to be used as a learned third learning model, and estimates and outputs distance information indicating the distance of the observation region by inputting the observation image 100 to the third learning model.

In addition, in this example, the near view mode and the distant view mode are included as a plurality of estimation modes for estimating the lesion region. Here, the distant view mode is a mode in which, in a case where the distance information exceeds a certain threshold value, the estimation accuracy of the lesion region is higher than that in the near view mode.

In a case where the processor 22 estimates the lesion region in the near view mode, the processor 22 applies the first parameter group to the learning model 23A read from the memory 23 to be used as a learning model (first learning model) that estimates the lesion region in the observation image 100 of the near view having the distance information less than the threshold value. The processor 22 estimates the lesion region in the observation image 100 of the near view by inputting the observation image 100 into the first learning model.

On the other hand, in a case where the processor 22 estimates the lesion region in the distant view mode, the processor 22 applies the second parameter group to the same learning model 23A read from the memory 23 to be used as a learning model (second learning model) that estimates the lesion region in the observation image 100 of the distant view having the distance information exceeding the threshold value. The processor 22 estimates the lesion region in the observation image 100 of the distant view by inputting the observation image 100 into the second learning model.

The first parameter group can be acquired by performing machine learning of unlearned learning model 23A by using a data set of a large number of learning data in which the observation image of the near view (see 5C of FIG. 5) and correct answer data (correct answer mask) indicating the lesion region are paired. Similarly, the second parameter group can be acquired by performing machine learning of unlearned learning model 23A by using the data set of a large number of learning data in which an observation image of a distant view (see 5A of FIG. 5) and correct answer data indicating a lesion region are paired.

Figure 7B:
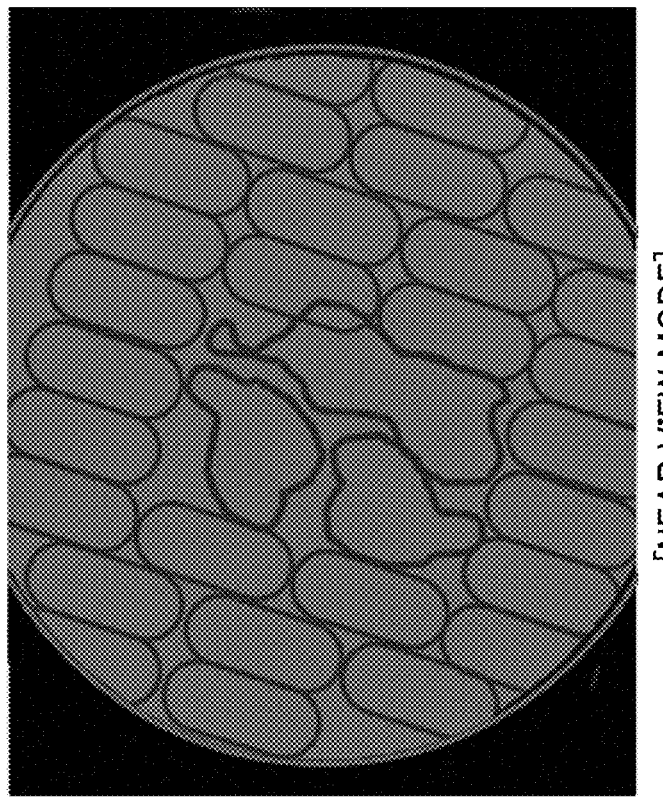
FIGS. 7A and 7B are diagrams showing an example of an observation image of a distant view to which a distant view mode is applied and an observation image of a near view to which a near view mode is applied.
Figure 7A:
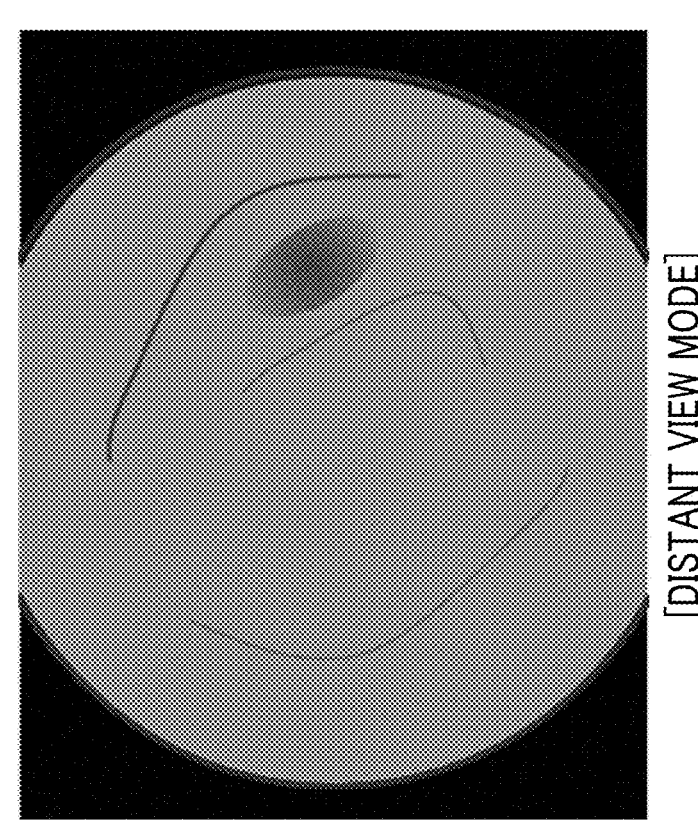

FIGS. 7A and 7B are diagrams showing an example of an observation image of a distant view to which a distant view mode is applied and an observation image of a near view to which a near view mode is applied.

In a case where the input observation image 100 is determined by the output of the third learning model for estimating the distance information to be the observation image 100 of the near view having the distance information less than the threshold value (in particular, in a case where the distance is uniform over the entire image as shown in FIG. 7B), the processor 22 selects the near view mode as the estimation mode for estimating the lesion region, and estimates the lesion region in the observation image 100 of the near view by using the first learning model corresponding to the selected near view mode.

In addition, in a case where the input observation image 100 is determined by the output of the third learning model for estimating the distance information to be the observation image 100 of a distant view having the distance information exceeding the threshold value (in particular, in a case where the distance is uniform over the entire image as shown in FIG. 7A), the processor 22 selects the distant view mode as the estimation mode for estimating the lesion region, and estimates the lesion region in the observation image 100 of the distant view by using the second learning model corresponding to the selected distant view mode.

Then, in a case where the near view mode is selected, the processor 22 uses the first learning model corresponding to the near view mode and estimates the lesion region in the observation image 100 of the near view to output the estimation result. In a case where the distant view mode is selected, the processor 22 uses a second learning model corresponding to the distant view mode (in this example, the parameter group used for the learning model 23A is switched from the first parameter group 23B to the second parameter group 23C), and estimates the lesion region in the observation image 100 of the distant view to output the estimation result.

The processor 22 switches the estimation mode (learning model to be used) depending on whether the observation image of the near view or the observation image of the distant view as described above, and without being limited in a case of outputting the estimation result of the lesion region, the estimation results of the lesion regions respectively estimated by the plurality of estimation modes (in this example, the near view mode and the distant view mode) may be weight-averaged according to the distance information of the observation image 100 to obtain the final output.

Figures 8A, 8B:
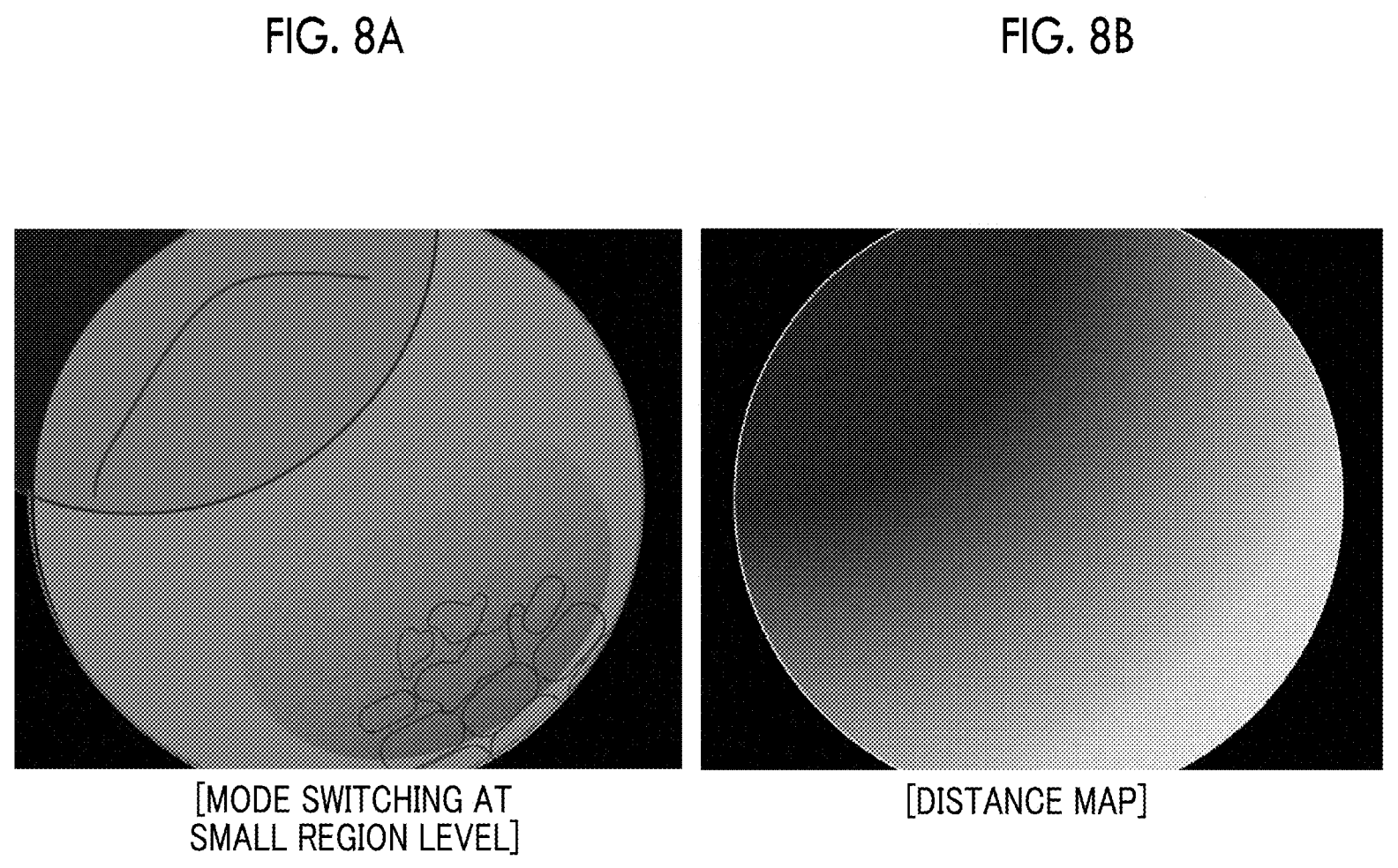

FIGS. 8A and 8B are diagrams showing an example of an observation image to which mode switching is applied in the observation image and a distance map showing distance information of an observation region of the observation image.

The observation image shown in FIG. 8A includes an observation region of a distant view in the upper left and an observation region of a near view in the lower right. In the distance map shown in FIG. 8A, pixel values are assigned that become blacker as the distance from the endoscope to the observation region increases and become whiter as the distance decreases.

In such an observation image, rather than applying the near view mode or the distant view mode to the entire image, it is preferable that the estimation mode to be applied in the observation image is switched between the near view mode and the distant view mode and applied.

In a case of this example, the processor 22 applies the distant view mode to the upper left region of the observation image shown in FIG. 8A, applies the near view mode to the other regions, and outputs the estimation results of the lesion region estimated in both estimation modes in an integrated manner.

The region of the observation image to which the near view mode or the distant view mode is applied includes regions such as one or more separated spots depending on the distance information of the observation region.

Figure 9C:
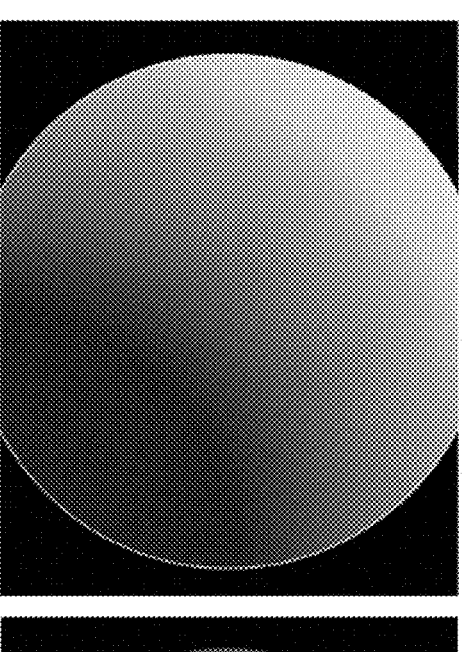
FIGS. 9A to 9C are diagrams showing a relationship between a switching pattern between the near view mode and the distant view mode and an estimation accuracy.
Figure 9B:
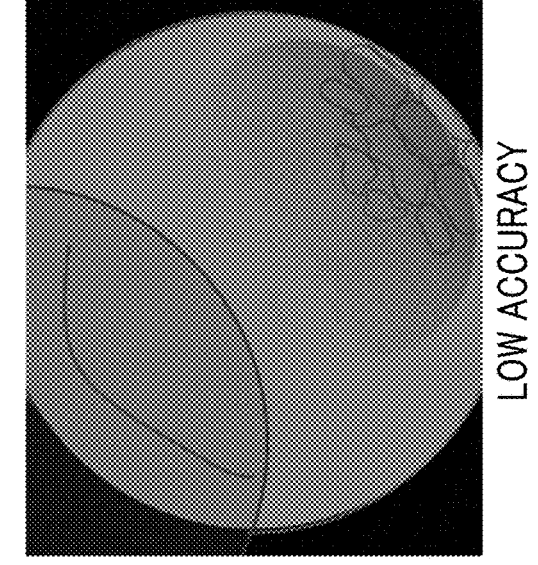
Figure 9A:
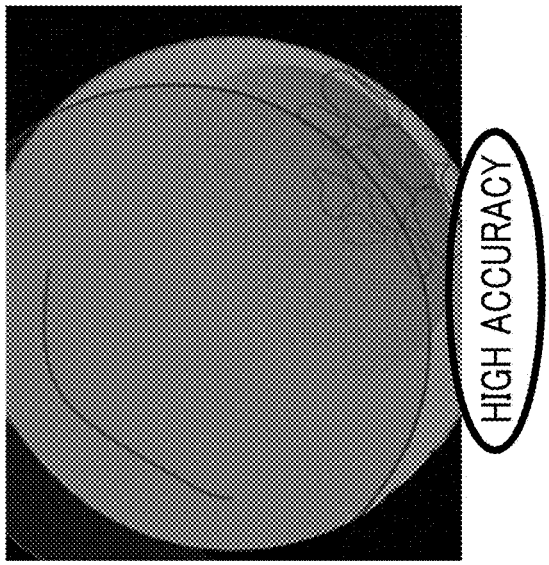

FIGS. 9A to 9C are diagrams showing a relationship between a switching pattern between the near view mode and the distant view mode and an estimation accuracy.

FIG. 9C is a distance map showing a distance from the endoscope to the observation region estimated from the observation image.

FIG. 9A shows a case in which a certain threshold value (first threshold value) is set for the distance information indicated by the distance map shown in FIG. 9C, the near view mode is applied to a region having distance information less than the first threshold value among the entire region of the observation image, the distant view mode is applied to the region having distance information exceeding the first threshold value, and the lesion region is estimated.

According to the switching pattern between the near view mode and the distant view mode shown in FIG. 9A, the region to which the distant view mode is applied is larger than the region to which the near view mode is applied.

On the other hand, FIG. 9B shows a case in which a threshold value (second threshold value) less than the first threshold value is set for the distance information indicated by the distance map shown in FIG. 9C, the near view mode is applied to the region having the distance information less than the second threshold value among the entire region of the observation image, the distant view mode is applied to the region having the distance information exceeding the second threshold value, and the lesion region is estimated.

According to the switching pattern between the near view mode and the distant view mode shown in FIG. 9B, the region to which the distant view mode is applied is smaller than the region to which the near view mode is applied.

In addition, the estimation result obtained by estimating the lesion region by applying the switching pattern shown in FIG. 9A is more accurate than the estimation result obtained by estimating the lesion region by applying the switching pattern shown in FIG. 9B.

Therefore, in a case of the observation image in this example, it is preferable to apply the switching pattern shown in FIG. 9A (that is, setting a region to which the near view mode is applied and a region to which the distant view mode is applied by the first threshold value).

In order to estimate the lesion region with higher accuracy, it is necessary to set an optimum switching pattern (that is, an optimum threshold value for dividing the region to which the near view mode and the distant view mode are applied). A method of determining the optimum threshold value in advance by trial and error, and a method of automatically estimating the optimum threshold value by a learning model for each observation image and using the estimated threshold value can be considered.

In this case, the learning model can be generated by performing machine learning on the unlearned learning model by using a data set of a large number of learning data in which an observation image and a threshold value (correct answer data) from which the estimation result of the lesion region with high accuracy is obtained for the observation image are paired.

Figures 10A, 10B, 10C:
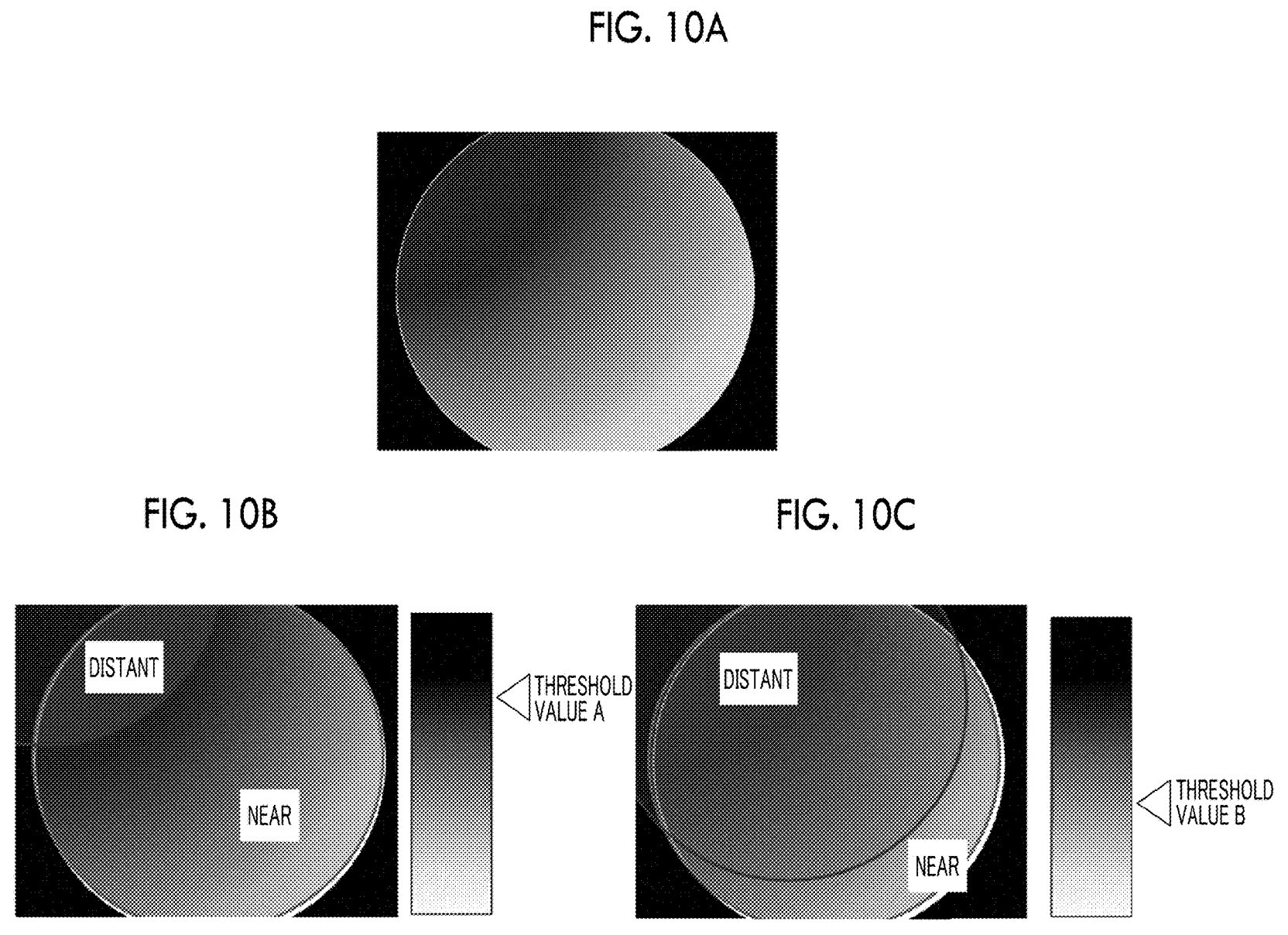

FIGS. 10A to 10C are diagrams showing an example of a user interface in a case where a user sets a switching pattern between the near view mode and the distant view mode.

FIG. 10A is a diagram showing an example of a distance map showing distance information of the observation region of the observation image.

As shown in FIGS. 10B and 10C, the processor 22 displays the distance map on the display device 40 and displays an operation screen having a slider (triangular icon) for setting a threshold value adjacent to the distance map.

The user can set a threshold value A shown in FIG. 10B and a threshold value B shown in FIG. 10C by moving the slider to a position of an arbitrary density (distance) by an operation unit 26, a touch panel (not shown), or the like.

In addition, as shown in FIGS. 10B and 10C, in a case where the threshold value A or the threshold value B set by the user is set, the processor 22 displays the region to which the near view mode is applied and the region to which the distant view mode is applied on the distance map according to the threshold value A or the threshold value B so as to be distinguishable by coloring or the like.

Accordingly, the user can confirm the switching pattern between the near view mode and the distant view mode according to the threshold value, and can set a desired switching pattern.

In addition, in the above example, the region to which the near view mode is applied and the region to which the distant view mode is applied are completely separated for the observation image, and the estimation result of the lesion region is acquired using the learning model corresponding to each mode. The present invention is not limited to this, the estimation result of the lesion region estimated in the near view mode and the estimation result of the lesion region estimated in the distant view mode may be weight-averaged according to the distance information to obtain the final output.

Figure 11C:
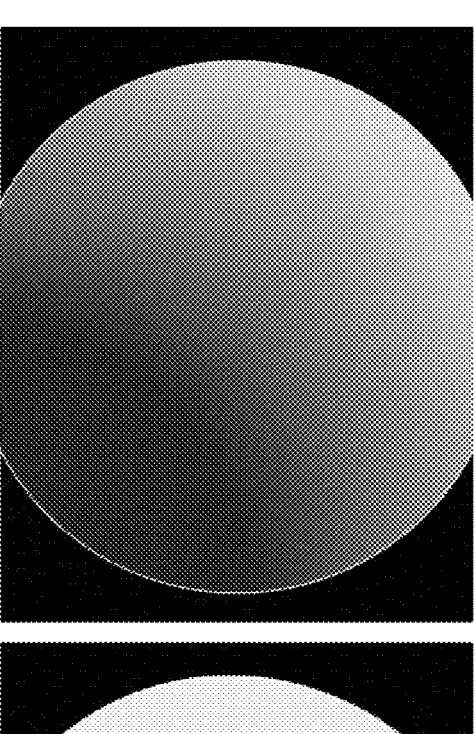
FIGS. 11A to 11C are diagrams showing an example of a weighting coefficient (near view ratio, distant view ratio) used for a weighted average of an estimation result of a lesion region estimated in a near view mode and an estimation result of a lesion region estimated in a distant view mode.
Figure 11B:
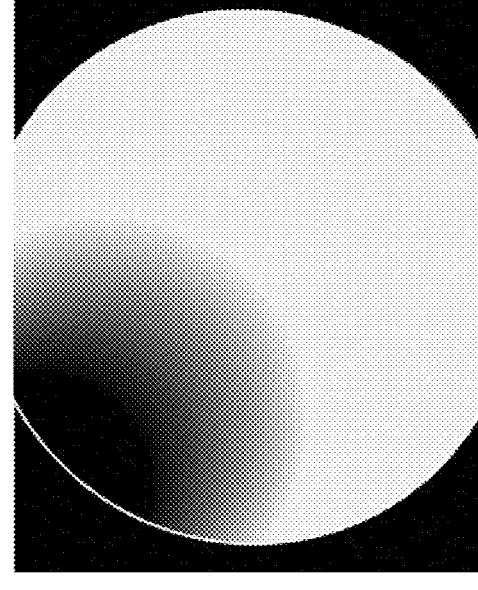
Figure 11A:
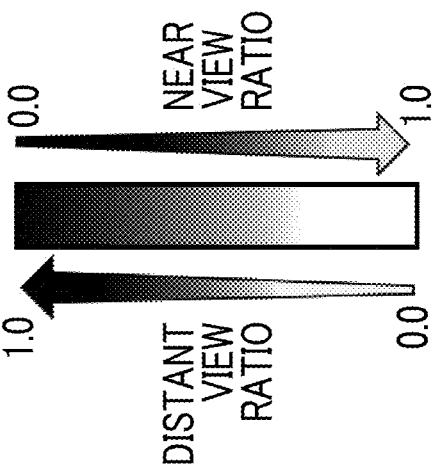

FIGS. 11A to 11C are diagrams showing an example of a weighting coefficient (near view ratio, distant view ratio) used for a weighted average of an estimation result of a lesion region estimated in a near view mode and an estimation result of a lesion region estimated in a distant view mode.

FIG. 11C is a diagram showing an example of a distance map showing distance information of the observation region of the observation image. The processor 22 obtains the near view ratio and the distant view ratio in pixel units based on the distance map. The near view ratio and the distant view ratio are not limited to the pixel unit, and may be obtained in a unit of a small region larger than one pixel.

As shown in FIG. 11A, the near view ratio and the distant view ratio of this example are values in a range of 0.0 to 1.0, respectively, and the total of the near view ratio and the distant view ratio obtained for a certain pixel is 1.0.

The processor 22 can use a learning model (fourth learning model) in which the distance map is used as an input and which outputs a weighting coefficient (near view ratio, distant view ratio) used in the calculation of the weighted average, input the distance map to the fourth learning model, and acquire the near view ratio and the distant view ratio for each pixel of the observation image from the fourth learning model.

FIG. 11B is an image diagram showing a near view ratio and a distant view ratio for each pixel of the observation image acquired based on the distance map of FIG. 11C.

In FIG. 6, the processor 22 can apply the fourth parameter group to the learning model 23A read from the memory 23 to be used as the learned fourth learning model, input the distance map to the fourth learning model, and acquire the near view ratio and the distant view ratio for each pixel of the observation image estimated by the fourth learning model.

In a case where the observation image is input instead of the distance map, the fourth learning model may be generated such that the near view ratio and the distant view ratio are estimated and output for each pixel of the observation image, or in a case where the both of the observation image and the distance map are input, the fourth learning model may be generated such that the near view ratio and the distant view ratio are estimated and output for each pixel of the observation image.

In addition, the processor 22 may acquire the near view ratio and the distant view ratio by reading out the near view ratio and the distant view ratio based on the distance information for each pixel from a look-up table in which the near view ratio and the distant view ratio are stored in advance according to the distance information without using the fourth learning model.

In a case where the estimation result of the lesion region estimated in the near view mode, the estimation result of the lesion region estimated in the distant view mode, and the near view ratio and the distant view ratio for each pixel of the observation image are acquired, the processor 22 calculates a weighted average based on the following equation.

$$\text{Weighted average}=(\text{estimation result by distant view mode})\times(\text{distant view ratio})+(\text{estimation result by near view mode})\times(\text{near view ratio}) \qquad \text{Equation 1}$$

The processor 22 causes the display device 40 on which the observation image 100 is displayed to display the estimation result (state of the observation region) of the lesion region obtained from the observation image 100 as described above. For example, in a case where a lesion region is detected from the observation image 100, the estimation result of the lesion region can be displayed on the display device 40 by superimposing and displaying a bounding box or the like surrounding the lesion region on the observation image 100.

Other Specific Examples of Processor of First Embodiment

Figure 12:
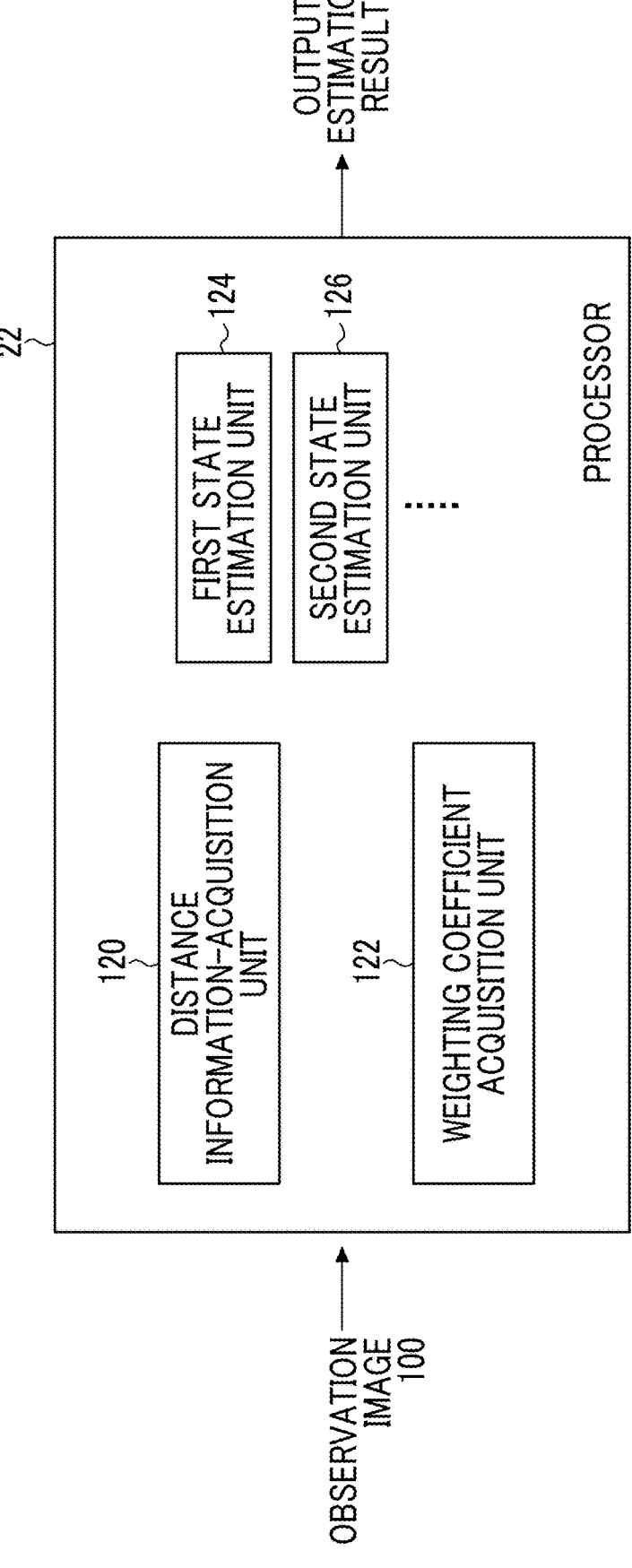
FIG. 12 is a block diagram showing another specific example of the processor shown in FIG. 3.

FIG. 12 is a block diagram showing another specific example of the processor shown in FIG. 3.

The processor 22 shown in FIG. 6 reads out the learning model 23A from the memory 23, and applies the first parameter group 23B, the second parameter group 23C, the third parameter group 23D, the fourth parameter group 23E, and the like, to the learning model 23A to operate the distance information-acquisition unit for acquiring the distance information, the weighting coefficient acquisition unit for acquiring the weighting coefficient used in weight-averaging the estimation result of the lesion region estimated in the near view mode and the estimation result of the lesion region estimated in the distant view mode, and the state estimation unit in the near view mode or in the distant view mode by switching the first parameter group 23B and the second parameter group 23C. The processor 22 shown in FIG. 12 is different from the processor 22 shown in FIG. 6 in that the processor 22 shown in FIG. 12 individually comprises a distance information-acquisition unit 120, a weighting coefficient acquisition unit 122, a first state estimation unit 124, a second state estimation unit 126, and the like.

Here, the first state estimation unit 124 and the second state estimation unit 126 use the learning models (first learning model, second learning model) to which the first parameter group 23B and the second parameter group 23C shown in FIG. 6 are applied, respectively, and the observation images 100 are input to the first learning model and the second learning model, respectively, to acquire the estimation result of the lesion region from the first learning model and the second learning model. Here, the first learning model can output the estimation result of the lesion region with high detection accuracy for the observation region in the near view for the input observation image 100, and the second learning model can output the estimation result of the lesion region with high detection accuracy for the observation region in the distant view for the input observation image 100.

The processor 22 selectively outputs any one of the estimation results of the lesion regions estimated by the first state estimation unit 124 and the second state estimation unit 126 with respect to the entire observation image 100, or integrally outputs the estimation results of the lesion regions selected in pixel units or small region units based on the distance information acquired by the distance information-acquisition unit 120, or weight-averages the estimation results of the lesion regions estimated by the first state estimation unit 124 and the second state estimation unit 126 according to the distance information of the observation image 100 to obtain a final output.

Second Embodiment of Processor

Figure 13:
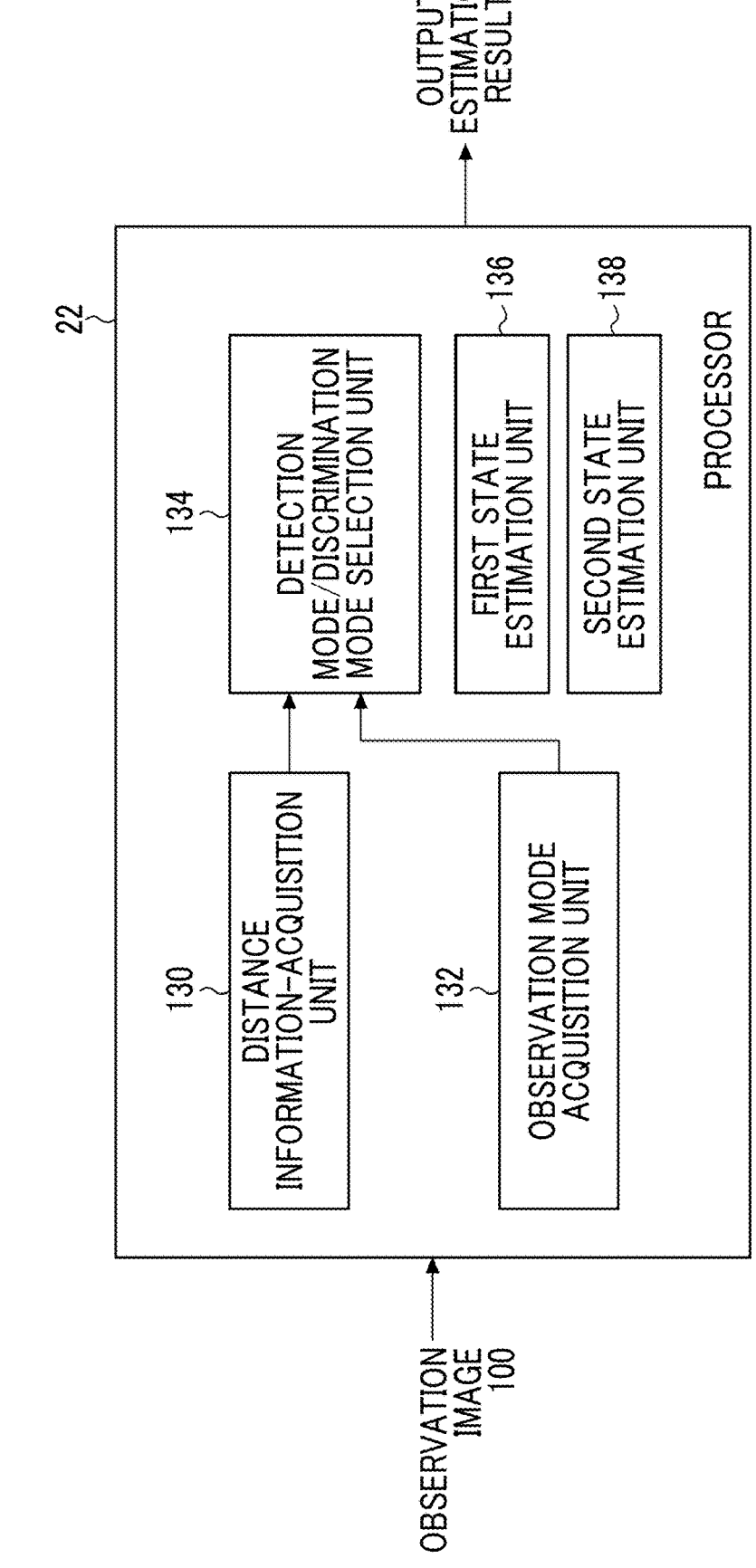
FIG. 13 is a functional block diagram showing a second embodiment of a main processor of the processor device shown in FIG. 2.

FIG. 13 is a functional block diagram showing a second embodiment of a main processor of the processor device shown in FIG. 2.

As shown in FIG. 13, the processor 22 comprises a distance information-acquisition unit 130, an observation mode acquisition unit 132, a detection mode/discrimination mode selection unit 134, a first state estimation unit 136, and a second state estimation unit 138.

The distance information-acquisition unit 130 is a portion that inputs the observation image 100 and acquires the distance information related to the distance from the endoscope to the observation region based on the input observation image 100, and outputs the acquired distance information to the detection mode/discrimination mode selection unit 134.

The observation mode acquisition unit 132 is a portion that acquires an observation mode indicating whether the observation image 100 is a normal light image or a special light image, and outputs an observation mode signal indicating the acquired current observation mode to the detection mode/discrimination mode selection unit 134.

The observation mode acquisition unit 132 can acquire the current observation mode by inputting, for example, an observation mode signal indicating an observation mode, which is a remote signal operated by a user in a hand operation unit of the endoscope 10.

The detection mode/discrimination mode selection unit 134 selects the detection mode or the discrimination mode based on the distance information and the observation mode to be input.

Here, the detection mode is one mode among a plurality of estimation modes, and is a mode for detecting a lesion (lesion region) existing in the observation region based on the observation image, and the discrimination mode is another mode among the plurality of estimation modes, and a mode in which lesions existing in the observation region are classified into two or more types of classes (for example, neoplastic and non-neoplastic) based on the observation image. The discrimination mode may include the detection mode, or may be a mode in which the lesion regions detected in the detection mode are individually classified into classes.

The detection mode/discrimination mode selection unit 134 selects the discrimination mode in a case where the distance information to be input is equal to or less than the threshold value and the observation mode is the special light observation mode for observing the special light image, and selects the detection mode in the other cases.

In a case where observation is performed using a special light image captured by using special light at a short distance in which the distance information is equal to or less than the threshold value, the user may desire to discriminate the lesion rather than detect the lesion. Accordingly, in a case such as "short-distance imaging and special light observation mode", it is preferable to select the discrimination mode. In addition, the observation image captured under the condition of "short-distance imaging and special light observation mode" is an image suitable for discrimination because the blood vessels and the structure of the mucosal surface layer of the subject are easily understood.

The first state estimation unit 136 is a state estimation unit that operates in a case where the detection mode is selected, and detects a lesion existing in the observation region based on the input observation image 100. The detection of the lesion (lesion region) by the first state estimation unit 136 can be performed using the learning model for detecting the lesion as described above. In addition, the first state estimation unit 136 may selectively acquire the estimation result of the lesion estimated in the near view mode and the distant view mode from the distance information, or may perform weight-averaging using the distance information to obtain the final output.

The second state estimation unit 138 is a state estimation unit that operates in a case where the discrimination mode is selected, and classifies lesions existing in the observation region into two or more types of classes based on the input observation image 100, and outputs the classified class (discrimination result).

The second state estimation unit 138 uses the learned learning model that is subjected to machine learning by using a data set of a large number of learning data in which a special light image captured at a short distance and a discrimination result (correct answer data) corresponding to the special light image are paired, inputs the observation image (a special light image captured at a short distance) to the learning model to output the discrimination result. In addition, the second state estimation unit 138 may classify classes of the lesions by using a support vector machine (SVM) which is a type of machine learning model.

The processor 22 selects the first state estimation unit 136 or the second state estimation unit 138 in accordance with the detection mode or the discrimination mode selected by the detection mode/discrimination mode selection unit 134, and displays the detection result or the discrimination result of the lesion estimated by the selected first state estimation unit 136 or second state estimation unit 138 on the display device 40 on which the observation image 100 is displayed. Accordingly, the user can confirm the detection result or the discrimination result of the lesion on the screen of the display device 40.

Operation Method of Medical Image Processing Device

Figure 14:
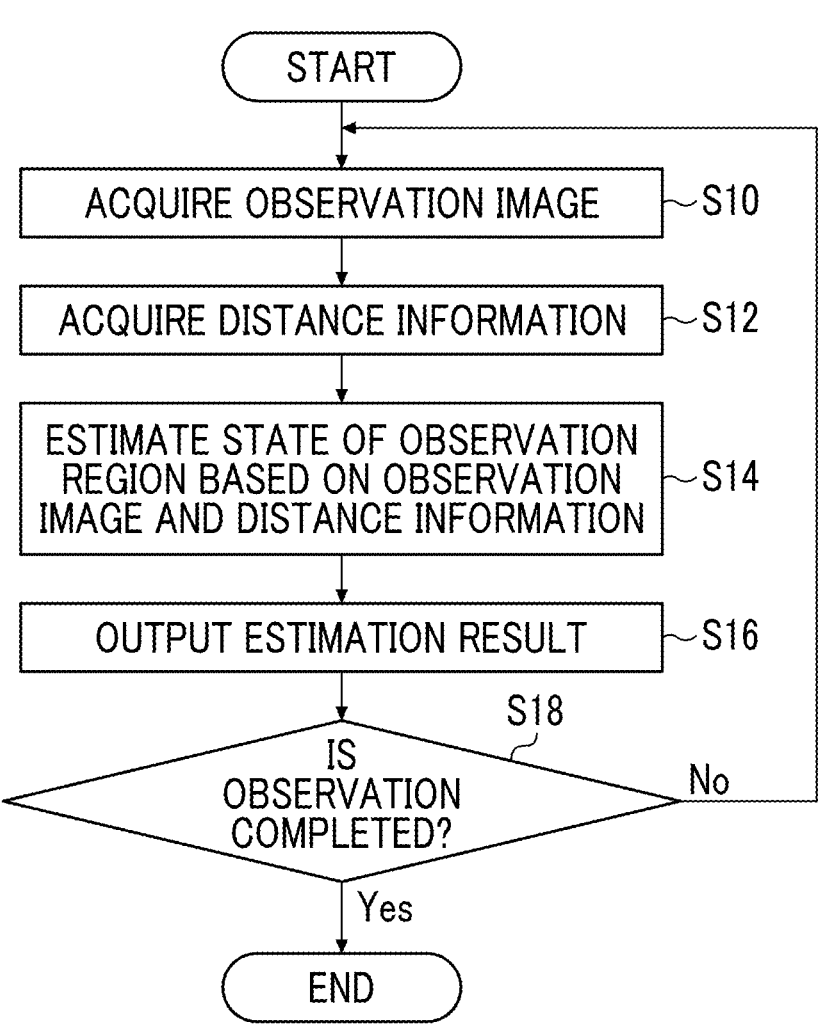
FIG. 14 is a flowchart showing an embodiment of an operation method of a medical image processing device according to the present invention.

FIG. 14 is a flowchart showing an embodiment of an operation method of the medical image processing device according to the embodiment of the present invention.

The operation method of the medical image processing device is, for example, a method of operating the medical image processing device comprising the processor 22 shown in FIG. 3, and the processor 22 executes various types of processing to be described below according to the flowchart shown in FIG. 14.

In FIG. 14, the processor 22 acquires an observation image in which an observation region in the body is imaged by the endoscope through the image acquisition unit 110 (step S10).

Subsequently, the processor 22 acquires distance information related to a distance from the endoscope to the observation region by the distance information-acquisition unit 112 (step S12). The distance information-acquisition unit 112 of this example uses a learning model (third learning model) that estimates the distance from the observation image, and inputs the observation image to the third learning model to acquire the distance information from the third learning model.

The processor 22 estimates a state of the observation region (for example, a lesion region existing in the observation region) based on the observation image acquired in step S10 and the distance information acquired in step S12 (step S14).

The state estimation unit 114 of the observation region of the processor 22 selects any estimation mode from a plurality of estimation modes (for example, near view mode and distant view mode) for estimating the lesion region based on the distance information, estimates the lesion region by the selected estimation mode, or weight-averages estimation results of the lesion region respectively estimated by the plurality of the estimation modes according to the acquired distance information to obtain the final output.

In addition, in step S12, in a case where each of pieces of distance information corresponding to a plurality of small regions in the observation region including the pixel unit of the observation image is acquired, in step S14 of estimating the state of the observation region (lesion region), each of states of each of the plurality of small regions in the observation region is estimated based on the observation image and the pieces of distance information corresponding to the plurality of small regions.

The processor 22 outputs the estimation result estimated in step S14 (step S16). It is preferable that the processor 22 displays the estimation result on the display device 40 that displays the observation image.

Subsequently, the processor 22 determines whether or not the observation of the observation image by the user is completed (step S18). In a case where a determination is made that the observation is not completed, a transition is made to step S10, and the processor 22 repeatedly executes the processing of steps S10 to S18. That is, in a case where the observation image is a moving image, the estimation result for the observation image of the moving image can be acquired in real time by repeatedly executing the processing of steps S10 to S18 every frame or every few frames. Determining whether the observation is completed can be performed, for example, by detecting a user operation that the user completes the endoscopy.

In step S18, the processor 22 determines that the observation is completed and completes the present processing.

Others

In the present embodiment, distance information regarding the distance from the endoscope to the observation region is acquired from the observation image by using AI. The present invention is not limited to this, for example, by using the laser beam or the like, in a case where the endoscope comprises a distance measuring unit that physically measures the distance between the distal end part of the endoscope and the observation target, the distance information measured by the distance measuring unit may be acquired.

Furthermore, in the present embodiment, two estimation modes, a near view mode and a distant view mode, have been described as a plurality of estimation modes applied according to the distance. The present invention is not limited to this, for example, the state of the observation region may be estimated for the observation images at the corresponding distances in three or more estimation modes including the intermediate view mode applied to the intermediate view between the near view and the distant view.

In addition, a hardware structure for executing various controls of the medical image processing device according to the embodiment of the present invention includes various processors illustrated as follows. The various processors include a central processing unit (CPU) that is a general-purpose processor functioning as various control units by executing software (program), a programmable logic device (PLD) such as a field programmable gate array (FPGA) that is a processor having a circuit configuration changeable after manufacturing, and a dedicated electric circuit or the like such as an application specific integrated circuit (ASIC) that is a processor having a circuit configuration dedicatedly designed to execute a specific type of processing.

One processing unit may be configured by one processor among these various processors, or may be configured by two or more same or different kinds of processors (for example, a combination of a plurality of FPGAs or a combination of the CPU and the FPGA). In addition, a plurality of control units may be configured with one processor. As an example of configuring the plurality of control units with one processor, first, as represented by a computer such as a client or a server, a form of configuring one processor with a combination of one or more CPUs and software and causing the processor to function as the plurality of control units is present. Second, as represented by a system on chip (SoC) or the like, a form of using a processor that implements the function of the entire system including the plurality of control units using one integrated circuit (IC) chip is present. Accordingly, various control units are configured using one or more of the various processors as the hardware structure.

In addition, the present invention includes a medical image processing program installed on the computer to cause the computer to function as the medical image processing device according to the embodiment of the present invention and a non-transitory computer-readable recording medium on which the medical image processing program is recorded.

Furthermore, the present invention is not limited to the above embodiment and can be subjected to various modifications without departing from the spirit of the present invention.

EXPLANATION OF REFERENCES

1: endoscope system
10: endoscope
20: processor device
21: image acquisition unit
22: processor
23: memory
23A: learning model
23B: first parameter group
23C: second parameter group
23D: third parameter group

19

23E: fourth parameter group
24: display control unit
25: input and output interface
26: operation unit
30: light source device
40: display device
100: observation image
110: image acquisition unit
112: distance information-acquisition unit
114: state estimation unit
120, 130: distance information-acquisition unit
122: weighting coefficient acquisition unit
124, 136: first state estimation unit
126, 138: second state estimation unit
132: observation mode acquisition unit
134: detection mode/discrimination mode selection unit
S10: step
S12: step
S14: step
S16: step
S18: step
What is claimed is:

1. A medical image processing device comprising a processor,
  wherein the processor
  acquires an observation image in which an observation region in a body is imaged by an endoscope,
  acquires distance information regarding a distance from the endoscope to the observation region, and
  estimates a state of the observation region based on the observation image and the distance information, wherein
  when a lesion exists in the observation region, the processor detects the lesion in the observation region as the state of the observation region and classifies the lesion existing in the observation region into two or more types of classes, and
  when a treatment tool exists in the observation region, the processor recognizes the treatment tool in the observation region or recognizes an organ or a part existing in the observation region,
  wherein the processor selects any estimation mode among a plurality of estimation modes for estimating the state of the observation region based on the acquired distance information, and estimates the state of the observation region by the selected estimation mode.

2. A medical image processing device comprising a processor,
  wherein the processor
  acquires an observation image in which an observation region in a body is imaged by an endoscope,
  acquires distance information regarding a distance from the endoscope to the observation region, and
  estimates a state of the observation region based on the observation image and the distance information, wherein
  when a lesion exists in the observation region, the processor detects the lesion in the observation region as the state of the observation region and classifies the lesion existing in the observation region into two or more types of classes, and
  when a treatment tool exists in the observation region, the processor recognizes the treatment tool in the observation region or recognizes an organ or a part existing in the observation region,
  wherein the processor weight-averages estimation results of the state of the observation region respectively estimated by a plurality of estimation modes for estimating the state of the observation region according to the acquired distance information to obtain a final output.

3. The medical image processing device according to claim 1, wherein the plurality of estimation modes include a near view mode in which the state of the observation region is estimated based on the observation image and a distant view mode in which the state of the observation region is estimated based on the observation image, and of which an accuracy of estimating the state of the observation region is higher than that of the near view mode in a case where the distance information exceeds a threshold value.

4. The medical image processing device according to claim 3,
  wherein a first learning model that uses the observation image as an input and estimates the state of the observation region corresponding to the near view mode, and a second learning model that uses the observation image as an input and estimates the state of the observation region corresponding to the distant view mode are provided, and
  the processor estimates the state of the observation region using at least one of the first learning model or the second learning model.

5. The medical image processing device according to claim 1, wherein the plurality of estimation modes include a detection mode in which a lesion existing in the observation region is detected based on the observation image, and a discrimination mode in which the lesion existing in the observation region is classified into two or more types of classes based on the observation image.

6. The medical image processing device according to claim 5,
  wherein the observation image includes a normal light image captured by using normal light and a special light image captured by using special light, and
  the processor
  acquires an observation mode indicating whether the observation image is the normal light image or the special light image together with the distance information of the observation image, and
  selects the detection mode or the discrimination mode based on the distance information and the observation mode.

7. The medical image processing device according to claim 6, wherein the processor selects the discrimination mode in a case where the distance information is equal to or less than a threshold value and the observation mode is a special light observation mode for observing the special light image.

8. The medical image processing device according to claim 1,
  wherein the processor
  acquires each of pieces of the distance information corresponding to a plurality of small regions in the observation region, and
  estimates each of states of the plurality of small regions in the observation region based on the observation image and the pieces of distance information corresponding to the plurality of small regions.

9. The medical image processing device according to claim 1,
  wherein a third learning model that uses the observation image as an input and estimates the distance information is provided, and the processor inputs the acquired observation image to the third learning model and acquires the distance information estimated by the third learning model.

10. The medical image processing device according to claim 2, wherein a fourth learning model that uses at least one of a distance map showing the distance information of the observation region of the observation image or the observation image as an input and outputs a weighting coefficient used in calculation of the weighted average is provided, and the processor inputs at least one of the distance map or the observation image to the fourth learning model, and acquires the weighting coefficient used in the calculation of the weighted average from the fourth learning model.

11. The medical image processing device according to claim 1, wherein the processor causes a display device that displays the observation image to display the estimated state of the observation region.

12. An operation method of a medical image processing device including a processor, the method comprising:

acquiring an observation image in which an observation region in a body is imaged by an endoscope by the processor;

acquiring distance information regarding a distance from the endoscope to the observation region by the processor; and estimating a state of the observation region based on the observation image and the distance information by the processor, wherein the method further comprises:

when a lesion exists in the observation region, detecting the lesion in the observation region as the state of the observation region and classifying the lesion existing in the observation region into two or more types of classes, by the processor, and when a treatment tool exists in the observation region, recognizing the treatment tool in the observation region or recognizes an organ or a part existing in the observation region, by the processor, wherein estimating the state of the observation region includes selecting any estimation mode among a plurality of estimation modes for estimating the state of the observation region based on the acquired distance information, and estimating the state of the observation region by the selected estimation mode.

13. The operation method of a medical image processing device according to claim 12, wherein in acquiring each of pieces of the distance information, the distance information corresponding to a plurality of small regions in the observation region is acquired, and in estimating the state of the observation region, each of states of the plurality of small regions in the observation region is estimated based on the observation image and the pieces of distance information corresponding to the plurality of small regions.

14. A non-transitory, computer-readable tangible recording medium on which a program for causing, when read by a computer, a processor provided to the computer to execute the operation method of a medical image processing device according to claim 12 is recorded.

* * * * *